United States Patent
Varma et al.

(10) Patent No.: US 6,451,957 B1
(45) Date of Patent: Sep. 17, 2002

(54) (HYDROXYALKYL)PHENOLS, METHOD FOR THEIR PREPARATION, AND USES THEREOF

(75) Inventors: Anjanikumar Jyotiprasad Varma, Pune (IN); Swaminathan Sivaram, Pune (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/684,795

(22) Filed: Oct. 10, 2000

Related U.S. Application Data

(63) Continuation-in-part of application No. 09/470,736, filed on Dec. 23, 1999.

(51) Int. Cl.[7] ............................................. C08G 64/00
(52) U.S. Cl. ...................................... 528/196; 528/198
(58) Field of Search ................................. 528/196, 198

(56) References Cited

U.S. PATENT DOCUMENTS 4,260,671 A  *  4/1981  Merrill ........................ 430/67

FOREIGN PATENT DOCUMENTS

| JP | 63-215751 | * | 9/1988 |
| JP | 63-215752 | * | 9/1988 |

OTHER PUBLICATIONS

Eberhard Neuse and J.D. Van Schalkwyk, South African Journal of Science, vol. 72, Aug. 1976, pp. 233–237.

* cited by examiner

*Primary Examiner*—Terressa M. Boykin
(74) *Attorney, Agent, or Firm*—Andrew J. Caruso; Noreen C. Johnson

(57) ABSTRACT

Hydroxyarylalkenes, particularly the ones constituting cashew nut shell liquid, are converted to (hydroxyalkyl) phenols, particularly 3-(8-hydroxy-noctyl)phenol, by ozonolysis followed by reduction, preferably with a hydride such as sodium borohydride. No protective acylation of the hydroxyarylalkenes is necessary. The resulting (hydroxyalkyl)phenols are useful for the preparation of polycarbonates.

16 Claims, No Drawings

(HYDROXYALKYL)PHENOLS, METHOD FOR THEIR PREPARATION, AND USES THEREOF

CROSS-REFERENCE TO RELATED APPLICATION

This application is a continuation-in-part of application Ser. No. 09/470,736, filed Dec. 23, 1999.

BACKGROUND OF THE INVENTION

This invention relates to 3-(hydroxyalkyl)phenols and a method for their preparation. More particularly, it relates to the preparation of 3-(8-hydroxy-n-octyl)phenol from cashew nut shell liquid.

Cashew nut shell liquid (hereinafter sometimes simply "CNSL" for brevity) has been known for years to contain compounds useful in various aspects of chemical industry, with particular reference to plastics production. It is of such interest for various purposes that technical grade distilled CNSL is a commercially available product. It comprises, in major proportion (typically about 80% by weight), a material also sold separately under the trade name CARDANOL which is a mixture of the hydroxyalkylphenols 3-(pentadec-8-enyl)phenol, 3-(pentadeca-8,11-dienyl)phenol and 3-(pentadeca-8,11,14-trienyl)phenol. Minor constituents include about 18% of a material also sold separately under the trade name CARDOL, which is a mixture of the corresponding 5-substituted resorcinols, and about 2% 2-methylcardol, which is a mixture of the corresponding 2-methyl-5-substituted resorcinols, and other materials not fully identified.

Among the structural studies performed on CNSL are isolation therefrom and chromatographic separation of esters, specifically the acetates, of the constituents of the CARDANOL mixture. According to Neuse et al., *S. Afr. J. Sci.*, 72, 233–237 (1976), these esters have undergone reaction with ozone followed by reduction with lithium aluminum hydride to produce 3-(8-hydroxy-n-octyl)phenyl acetate. However, it does not appear that the acetate was converted to the corresponding 3-(8-hydroxy-n-octyl)phenol (hereinafter sometimes designated "HOP" for brevity), which therefore appears to be a novel compound. The disclosed reaction sequence is, of course, unsuited to commercial production of HOP; in fact, it was performed by Neuse et al. only for structure determination. Nor does it appear to be suggested in the prior art that HOP can be employed in the synthesis of polycarbonates.

Aromatic polycarbonates and polyesters, as represented by 2-2-bis(4-hydroxyphenyl)propane (bisphenol A) polycarbonate, are a widely used class of generally amorphous polymers characterized by such properties as transparency, durability, high impact resistance and solvent resistance. Corresponding aliphatic polymers are also known; many of them, especially the polycarbonates, are semicrystalline materials with low melting points and are frequently used as plasticizers. Copolymers containing aliphatic carbonate units in combination with aromatic polycarbonate or urethane units are of interest because of their significantly lower softening and melting points than those of the corresponding wholly aromatic polymers.

It is known to incorporate aliphatic structural units in otherwise aromatic polycarbonates and polyesters, either by way of comonomers or as physical blends, to afford materials with lower melting points than purely aromatic polycarbonates. It is also known to prepare aromatic polycarbonates and polyesters with varied properties by modifying the molecular structures of the dihydroxy compounds employed in their synthesis. For example, the use as comonomers of dihydroxyaromatic compounds having long chain aliphatic substituents can afford polycarbonates with high flow and improved impact resistance.

A substantially simpler preparation method is necessary to afford HOP and analogous (hydroxyalkyl)phenols in amounts suitable for commercial use, as polycarbonate and polyester precursors and for other purposes.

SUMMARY OF THE INVENTION

The present invention provides a simple method for conversion of CNSL to 3-(hydroxyalkyl)phenols. It is based on the discovery that ozonolysis can conveniently be performed on unresolved CNSL and followed by reduction, to produce a mixture of compounds including the corresponding (hydroxyalkyl)phenols. The additional, undesirable step of esterifying the phenolic hydroxy group is not necessary.

One aspect of the invention is the compound 3-8-hydroxyn-octyl)phenol.

Another aspect is a method for preparing a (hydroxyalkyl)phenol which comprises:

contacting ozone under reactive conditions with a reactant comprising at least one hydroxyarylalkene to produce an ozonolysis product, and reducing said ozonolysis product.

In a preferred embodiment of the invention, said reactant is CNSL comprising a major proportion of at least one of the hydroxyalkylphenols 3-(pentadec-8-enyl)phenol, 3-(pentadec-8,11-dienyl)phenol and 3-(pentadec-8,11,14-trienyl)phenol.

Still another aspect of the invention is a polycarbonate comprising (hydroxyalkyl)phenol- and particularly HOP-derived structural units, optionally in combination with units derived from other bisphenols such as bisphenol A.

DETAILED DESCRIPTION; PREFERRED EMBODIMENTS

An essential reactant employed in the method of this invention is at least one hydroxyarylalkene. It may be a single compound, but a principal advantage of the invention is its applicability to mixtures containing a plurality of hydroxyarylalkenes without the necessity of separating the constituents of said mixtures. CNSL, by reason of its availability and particular chemical suitability, is a preferred mixture of this type. For the sake of brevity, the reactant frequently identified hereinafter will be CNSL, but it should be understood that other hydroxyarylalkenes, as single compounds or mixture constituents, may be substituted therefor.

CNSL may be employed without any type of chemical treatment such as protective acylation of the phenolic hydroxy group. However, it is frequently preferred to distill the CNSL prior to performing further operations. Technical grade distilled CNSL is suitable.

According to the invention, the CNSL is contacted with ozone, $O_3$. Conventional ozonolysis conditions are employed. Thus, the ozone may be produced by silent electrical discharge and employed in admixture with one or more other gases, typically molecular oxygen, $O_2$. The temperature of contact is typically between about −20° and about 10° C., most often from about −10° to about 0° C. Substantially inert solvents, typically halogenated hydrocarbons and especially chlorinated aliphatic hydrocarbons such as chloroform and methylene chloride, may be employed as diluents.

The products of the ozonolysis reaction may be further converted to (hydroxyalkyl)phenols, specifically HOP, by reduction. Any suitable reducing agent capable of converting ozonolysis products to alcohols may be employed, with inorganic hydrides such as lithium aluminum hydride, sodium borohydride and dialkylaluminum hydrides such as diisobutylaluminum hydride often being employed as reducing agents. Diisobutylaluminum hydride and the like are often preferred by reason of ease of handling, being a liquid and soluble in organic solvents such as toluene. It is also within the scope of the invention to employ for reduction a hydrogenolysis reaction; i.e., contact with hydrogen in the presence of a catalyst such as copper chromite. Suitable solvents may be employed, including alkanols such as ethanol in the case of sodium borohydride, and reduction temperatures may be in the range of about 30–60° C.

Isolation of the ozonolysis product prior to reduction is not necessary and is usually not preferred. Rather, the entire ozonolysis product may be reduced. After reduction, separation of the desired (hydroxyalkyl)phenol from other ozonolysis-reduction products, including the analogous resorcinols, may be achieved by conventional means such as column chromatography.

The (hydroxyalkyl)phenols obtained by the method of this invention may be converted to homo- or copolycarbonates and homo- and copolyesters by art-recognized methods, including art-recognized interfacial and transesterification methods (i.e., reaction with phosgene and diaryl carbonates respectively) optionally in combination with solid state polymerization. Copolycarbonates and copolyesters of the invention have lower melting points than corresponding polycarbonates not containing (hydroxyalkyl)phenol-derived units.

The invention is illustrated by the following examples. All percentages are by weight.

EXAMPLE 1

A solution of 5.04 g of vacuum distilled commercial CNSL in 50 ml of chloroform was cooled to 0° C. in an ice bath and ozone was passed through for 45 min at 0.65 mol/hr. The solution was flushed with nitrogen for 10 minutes and transferred to a 2-liter three-necked flask fitted with a condenser, stirrer and addition funnel. A solution of 6.4 g of sodium borohydride in 50 ml of 50% aqueous ethanol solution was introduced at a temperature of 5–10° C. over 45 minutes, with stirring. The mixture was warmed to 40° C. and stirred for 2 hours, after which the pH was reduced to 2–4 by addition of 10% aqueous sulfuric acid solution.

The aqueous and organic layers were separated and the aqueous layer was extracted with chloroform. The combined organic layers were dried over sodium sulfate and filtered. The solvent was removed by distillation to yield 5 g of crude product which was eluted by column chromatography over silica gel using a mixture of 9 parts of petroleum ether and 1 part of ethyl acetate. There was obtained 3 g of pure HOP; its structure was confirmed by proton nuclear magnetic resonance spectroscopy.

EXAMPLE 2

A solution of 50.2 g of vacuum distilled commercial CNSL in 200 ml of chloroform was cooled to −8° C. in an ice-salt bath and ozone was passed through for 6 hr at 0.65 mol/hr. The solution was transferred to a 2-liter three-necked flask fitted with a condenser, stirrer and addition funnel. A solution of 64 g of sodium borohydride in 200 ml of 50% aqueous ethanol solution was introduced at a temperature of 10"15° C. over 2.5 hrs, with stirring. The mixture was warmed to 50° C. and stirred for 2.5 hours, after which the pH was reduced to 3–4 by addition of 10% aqueous sulfuric acid solution.

The aqueous and organic layers were separated and the aqueous layer was extracted with chloroform. The combined organic layers were dried over sodium sulfate and filtered. The solvent was removed by distillation to yield 54 g of crude product which was eluted by column chromatography over silica gel using a mixture of 9 parts of petroleum ether and 1 part of ethyl acetate. There was obtained 30 g of pure HOP.

EXAMPLE 3

A round-bottomed flask fitted with a condenser and nitrogen inlet was charged with 2.5536 g of bisphenol A, 437.9 mg of HOP (85:15 weight ratio), 5.6282 g of diphenyl carbonate and 3.5 mg of bisphenol A disodium salt as an internal standard. The reaction mixture was heated in a nitrogen atmosphere at 180° C. for 3 hours, with stirring. The temperature was then raised to 240° C. and vacuum was applied. After 2.5 hours, the temperature was further increased to 250° C. and heating was continued for one hour. The mixture was cooled, dissolved in chloroform and precipitated into methanol. The precipitate was filtered and dried in vacuum at 40° C. It was shown by proton nuclear magnetic resonance spectroscopy to be the desired copolymer of bisphenol A and HOP, having an intrinsic viscosity of 0.24 dl/g and a glass transition temperature of 85° C.

What is claimed is:

1. 1.3-(8-Hydroxy-n-octyl)phenol.
2. A method for preparing a (hydroxyalkyl)phenol which comprises:

contacting ozone under reactive conditions with a reactant comprising at least one hydroxyarylalkene to produce an ozonolysis product, and reducing said ozonolysis product.

3. A method according to claim 2 wherein the reactant is cashew nut shell liquid comprising a major proportion of at least one of the hydroxyalkylphenols 3-(pentadec-8-enyl)phenol, 3-(pentadec-8,11-dienyl)phenol and 3-(pentadec-8,11,14-trienyl)phenol.
4. A method according to claim 1 wherein the cashew nut shell liquid has been distilled.
5. A method according to claim 4 wherein said ozonolysis product is reduced by contact with an inorganic hydride.
6. A method according to claim 5 wherein the inorganic hydride is lithium aluminum hydride.
7. A method according to claim 5 wherein the inorganic hydride is sodium borohydride.
8. A method according to claim 5 wherein the inorganic hydride is a dialkylaluminum hydride.
9. A method according to claim 4 wherein said ozonolysis product is reduced by catalytic hydrogenolysis.
10. A method according to claim 9 wherein said hydrogenolysis is in the presence of copper chromite as catalyst.
11. A method for preparing 3-(8-hydroxy-n-octyl)phenol which comprises:

contacting ozone under reactive conditions with cashew nut shell liquid comprising a major proportion of at least one of the hydroxyalkylphenols 3-(pentadec-8-enyl)phenol, 3-(pentadec-8,11-dienyl)phenol and 3-(pentadec-8,11,14-trienyl)phenol to produce an ozonolysis product, and reducing said ozonolysis product with an inorganic hydride.

12. A polycarbonate comprising (hydroxyalkyl)phenol-derived structural units.

13. A polycarbonate according to claim 12 comprising 3-(8-hydroxy-noctyl)phenol-derived structural units.

14. A polycarbonate according to claim 12 which s a copolycarbonate.

15. A copolycarbonate according to claim 14 comprising bisphenol A structural units.

16. A copolycarbonate according to claim 15 wherein the (hydroxyalkyl)phenol-derived structural units are derived from 3-(8-hydroxy-n-octyl)phenol.

* * * * *